United States Patent [19]
Halling

[11] Patent Number: 5,772,598
[45] Date of Patent: Jun. 30, 1998

[54] DEVICE FOR TRANSILLUMINATION

[75] Inventor: Horst Halling, Pier, Germany

[73] Assignee: Forschungszentrum Julich GmbH, Julich, Germany

[21] Appl. No.: 652,569

[22] PCT Filed: Dec. 15, 1994

[86] PCT No.: PCT/DE94/01492

§ 371 Date: May 29, 1996

§ 102(e) Date: May 29, 1996

[87] PCT Pub. No.: WO95/16908

PCT Pub. Date: Jun. 22, 1995

[30] Foreign Application Priority Data

Dec. 15, 1993 [DE] Germany .................. 43 42 526.7

[51] Int. Cl.$^6$ ...................................................... A61B 6/00
[52] U.S. Cl. ................................................................ 600/476
[58] Field of Search ................... 128/633, 664, 128/665; 73/865.8; 250/330, 341.1, 358.1; 356/335–338, 341; 600/473, 476

[56] References Cited

U.S. PATENT DOCUMENTS

| | | | |
|---|---|---|---|
| 3,674,008 | 7/1972 | Johnson | 128/665 |
| 4,281,645 | 8/1981 | Jöbsis | 128/633 |
| 4,495,949 | 1/1985 | Stoller | 128/664 |
| 5,371,368 | 12/1994 | Alfano et al. | 128/664 |
| 5,419,320 | 5/1995 | Kawaguchi | 128/633 |
| 5,451,785 | 9/1995 | Faris | 128/664 |

FOREIGN PATENT DOCUMENTS

| | | |
|---|---|---|
| 0 585 620 A1 | 9/1994 | European Pat. Off. . |
| 2092856 | 8/1982 | United Kingdom . |

OTHER PUBLICATIONS

"Edge Inspection of Semiconductor Substrates", Technical Disclosure Bulletin vol. 33, No. 4, Sep. 1990.

"Reticle Inspection Using Diffraction Pattern Masking", Xerox Disclosure Journal, vol. 9, No. 1, Jan./Feb. 1984.

*Primary Examiner*—Lee S. Cohen
*Assistant Examiner*—Bryan K. Yarnell
*Attorney, Agent, or Firm*—Herbert Dubno

[57] ABSTRACT

Human or other tissue is transluminated by light from a coded aperture and focussed on a focal plane in which the object is positioned. The light traversing the light is collimated and a light-sensitive detector and image processor collects the collimated light.

3 Claims, 2 Drawing Sheets

CODE WITHOUT
SCATTERING LIGHT

CODE WITH SCATTERING
LIGHT

CODE WEAKENED
THROUGH STRONGER

DEVICE FOR TRANSILLUMINATION

CROSS REFERENCE TO RELATED APPLICATION

This application is a national phase of PCT/DE94/1492 which is based upon German national application P4342526.7 of 15 Dec. 1993 under the International Convention.

FIELD OF THE INVENTION

The invention relates to a device for the translumination of an object.

1. Background of the Invention

When a diffuse scatterer, for example human tissue of the hand, is transluminated with light of high intensity it appears to be translucent. In a disadvantageous manner, however, the local resolution is very poor and is not suitable to provide an information-rich, location-dependent, image-true reproduction of the scatterer.

It is the object of the present invention to provide a device for transluminating an object with especially visible light with high local resolution.

SUMMARY OF THE INVENTION

The object is achieved with a device having a code aperture through which parallel light can pass, means for focussing this coded light, an object in the focal plane of the focussed light, means for collimating the light traversing the object, and a light-sensitive detector collecting this light.

In particular, the device has means with the aid of which parallel light passes through a coded aperture and this light is then focussed. The object to be transluminated is positioned in the focal plane of the focussed light. Means can then be provided which allows a scanning within the focal plane by shifting it relative to the transluminated object (the diffuse scatterer).

2. Object of the Invention

The invention further has means for collimating the light passing through the object. Finally, a light-sensitive detector is provided which collects the so-collimated light. The detector signal is thus applied to an electronic image processor. As a result, even with diffusion scattering, a high local resolution of the scatterer (as for example the human hand) can be obtained. A preferred embodiment has, means for shifting in the focal plane for the purpose of selective translumination of individual regions of the object. Thus the diffuse scatterer can be repeatedly scanned to yield, in total, a complete image of the transluminated objects by joining the individual signals from local scanning.

An advantages embodiment of the invention is provided when a coding pattern is provided in the aperture which permits cross correlation in the evolution of the measured detector signal.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
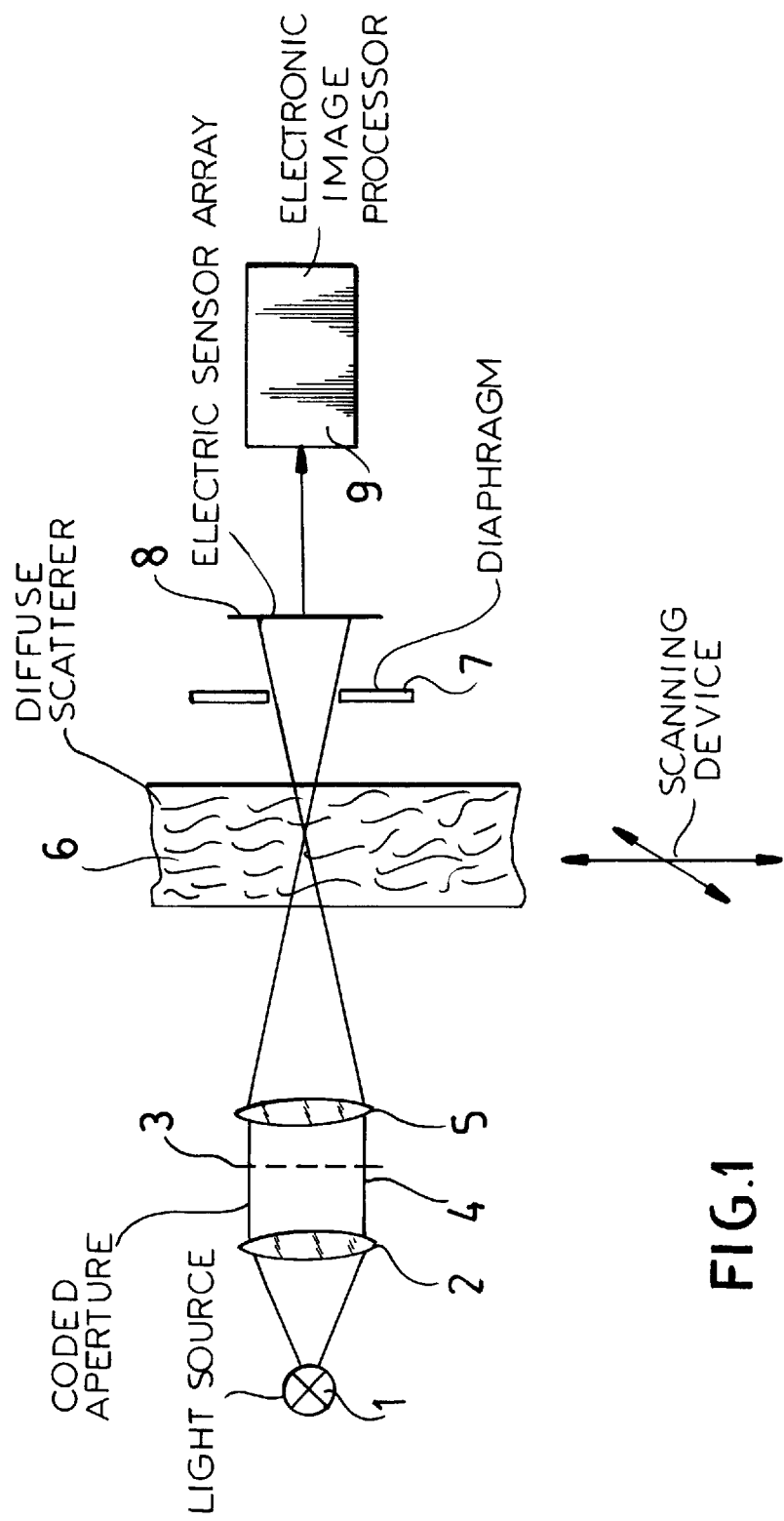
FIG. 1 is a schematic illustration of the individual components of the device according to the invention along the light path from the source of the detector.

The device shown in FIG. 1 has a light source 1 which is so positioned in the focal plane of a lens 2 that downstream of this lens parallel light emerges from this lens 2 and passes through a coded aperture 4 and is then focussed by a further lens 5. In the focal plane of the lens 5, a diffuse scatterer 6 to be transluminated is positioned. The light passing through the latter impinges, after traversing a diaphragm 7 for collimation, upon a detector 8, especially a sensor array 8. From there the electrical signal which is picked up is fed to an electronic image processor 9. The device is a scanning device not shown in detail which enables the shifting of the diffuse scatterer 6 in the focal plane of the lens 5 so that successive scannings of the object can be achieved with the aid of this device.

In particular, the light source 1 is chosen which has the highest possible light intensity. The coded aperture 4 contains a predetermined pattern of openings in the aperture plane. The electronic detector 8 can be, for example, a CCD charged coupled device or a diode array. According to the process the object 6 to be investigated is illuminated with the patterned light through the aperture 4 in the focal plane and is scanned repeatedly, whereby the individual information obtained at the detector 8 during scanning can be assembled into a complete picture electronically. Below the measurement in detail at one point of the object is described in greater detail.

If there is no diffuse scatterer in the radiation path, the pattern of the aperture is obtained as a result at the detector. This pattern is so chosen that a counter-pattern exists in the electronic evaluation whose cross correlation with the pattern has a single distinctive maximum. It is known that in the case of translumination of a diffuser at a certain location, diffuse scattering components arise which appear as a "veil" superimposed upon the pattern of the aperture. The scattered light is, however, not patterned since this scattering is effected uncorrelated to the pattern. To the extent that the cross correlation is effected electronically and pattern and scattered light are not superposed, the nonpatterned component is suppressed by the cross correlation.

In the cross correlation, the uncorrelated nonpatterned light makes no contribution to the maximum signal. More commonly, the contribution to the uncorrelated light with respect to the contribution of the correlated is negligibly small. The two-dimensional cross correlation function $$\Phi_{xy} = \Sigma_{lk} x[n+l, n+k] \times y[l,k]$$

between the mask and received image is used. For a given thickness of the scatterer, the height of the maximum of the light intensity measured at the detector, is a measure of the light absorption in the scatterer.

One starts from the assumption that in the scatterer there are small regions with increased light absorption which should be found. A typical example in this connection can be a wood splinter in the hand to be transluminated.

By scanning the interesting region of the object, one finds with high resolution the location with increased light absorption since a maximum of the cross correlation function is smaller than in a neighboring region.

Figure 2A:
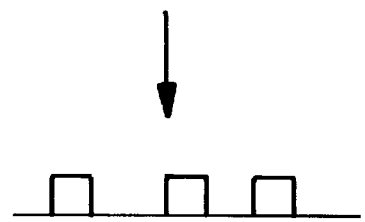
FIG. 2a is a plot of the intensity of the light as a function of the location of the receiver for the code without scattered light.
Figure 2B:
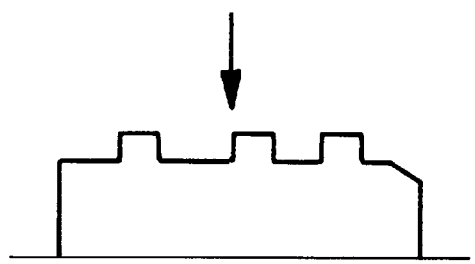
FIG. 2b is a plot of the intensity of the light as a function of location at the receiver for the code with scattered light with weak absorption.
Figure 2C:
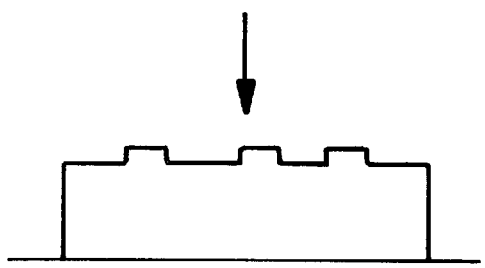
FIG. 2c is a plot of the intensity of the light as a function of location at receiver for a weakened code with stronger absorption.

As is apparent from FIG. 2a, the signal collected from the detector indicates a coding which corresponds to the patterning of the aperture in the case in which no scatterer is positioned in the device. In FIGS. 2b and 2c, the case is shown of the translumination of an object in the focal plane of the lens 5 of the device according to the invention, having a modified patterning (code), which also contains a scattering component which is weakened to a greater extent (FIG. 2c) or to a lesser extent (FIG. 2b) depending upon the more or less strong absorption in the diffuse scatterer at the local position. In particular, it is advantageous for practical utilization to so form the device that the measuring time per scanning point of the transluminated object is as small as possible, for example within 1 ms. In this case, a scanning area of 100×100 mm$^2$ can be scanned within about 10 seconds to enable an image of the object to be obtained.

One can consider, in carrying out the scatter measurements of the scattering object to shift the latter with the aid of a scanning device. However it is also conceivable, with a fixedly positioned scatterer to shift the apparatus correspondingly during the scanning. Such a shifting can be effected mechanically or also optically without mechanical shifting of the light source, aperture and detector.

It is advantageous to utilize as the light one which has a predetermined wavelength which is as large as possible. It is thus conceivable to provide a light source which operates in the infrared range.

The coded aperture and the means for focusing the coded light can also be realized in that the light can be directed from an arrangement of a plurality of glass fibers which are so arranged with respect to one another that from the light outlet side of this glass fiber bundle, a converging light bundle is obtained having the desired definite pattern as a result of the arrangement of the glass fibers. In this manner, the device of the invention can have the light entry side of the diffuse scatterer a light source rendered in glass fiber technology and thus in an advantageous manner, compact and, by comparison to optical lens systems, free from drawbacks associated with such lens systems.

In a corresponding way, such a glass fiber arrangement can be provided at the light outlet side of the diffuse scatterer and light traversing the scatterer can be collected with the aid of an arrangement of glass fibers converging toward the scatterer and conducted to the detector especially the sensor array, selectively.

It is then highly advantageous if each individual glass fiber at the light inlet side of the scatterer is provided with a glass fiber at the light outlet side of the scatterer to collect and further guide the light from the glass fiber at the inlet side. At the light outlet side of the scatterer, glass fibers are provided which have a three-dimensional orientation at their ends neighboring the scatterer. As a result the component which is not scattered at the diffuse scatterer from the glass fiber at the light inlet side emerges and passes through the region of the scatterer to be investigated with the scatterer-traversing light then impinging upon the ends of the glass fibers at the light outlet side of the scatterer, in this manner being collected and further guided.

The device is suitable for transluminating human tissue especially in the field of mammography and can advantageously replace previously known processes utilizing X-radiation illumination to a certain degree. It is also advantageous to utilize the device where nonhuman tissue is transluminated and thus investigated.

I claim:

1. A device for transluminating an object containing tissue and capable of diffuse scattering of transluminating light, said device comprising:

a source of light capable of transluminating said object;

a coded aperture through which a parallel beam of light from said source is passed said beam traveling along a path;

means in the path of the beam passing through said coded aperture for focussing coded light therefrom;

means for positioning said object at a focal plane of the focussed light;

means for collimating light transversing said object; and a light-sensitive detector and image processor for collecting collimating light, said light beam being coded with a pattern enabling evaluation of signals from said detector for cross correlation.

2. The device defined in claim 1, further comprising means for shifting said object relative to said beam for selectively transluminating individual regions of said object in said focal plane.

3. The device defined in claim 1 wherein said coded aperture and said means for focussing includes a multiplicity of glass fibers training individual rays of said light in a converging coded light bundle.

\* \* \* \* \*